United States Patent [19]

Iezzi et al.

[11] Patent Number: 5,633,421
[45] Date of Patent: May 27, 1997

[54] PROCESS FOR DEHYDROGENATING LIGHT PARAFFINS IN A FLUIDIZED BED REACTOR

[75] Inventors: Rodolfo Iezzi; Andrea Bartolini, both of San Donato Milanese, Italy

[73] Assignees: Eniricerche S.p.A.; Snamprogetti S.p.A., both of Milan, Italy

[21] Appl. No.: 392,616

[22] Filed: Feb. 22, 1995

Related U.S. Application Data

[63] Continuation of Ser. No. 76,644, Jun. 15, 1993, abandoned.

[30] Foreign Application Priority Data

Jun. 23, 1992 [IT] Italy ................ MI92A1535

[51] Int. Cl.$^6$ ................ C07C 5/327; C07C 5/333
[52] U.S. Cl. ................ 585/660; 585/654
[58] Field of Search ................ 585/634, 659, 585/660, 661; 502/38, 41

[56] References Cited

U.S. PATENT DOCUMENTS

| | | | |
|---|---|---|---|
| 2,672,490 | 3/1954 | Roetheli | 585/659 |
| 4,172,853 | 10/1979 | Antos | 585/379 |
| 4,902,849 | 2/1990 | McKay et al. | 585/660 |
| 4,996,387 | 2/1991 | Gerhold et al. | 585/660 |
| 5,030,338 | 7/1991 | Harandi et al. | 585/660 |
| 5,087,792 | 2/1992 | Cottrell et al. | 585/661 |

FOREIGN PATENT DOCUMENTS

| | | |
|---|---|---|
| 328507 | 8/1989 | European Pat. Off. . |
| 441430 | 8/1991 | European Pat. Off. . |
| 3312515 | 10/1983 | Germany . |

*Primary Examiner*—Ponnathapura Achutamurthy
*Attorney, Agent, or Firm*—Oblon, Spivak, McClelland, Maier & Neustadt, P.C.

[57] ABSTRACT

A process for dehydrogenating light paraffins, in particular $C_2$-$C_5$, to obtain the corresponding light olefins, comprising reacting said paraffins with a catalytic system containing platinum, tin and an alumina support and possibly an element of the lanthanide group in a fluidized bed reactor, where the heat required for the reaction is provided by said catalytic system as sensible heat, operating at a temperature of between 500° and 700° C. and at a pressure of between 1 and 2 kg/cm$^2$, and regenerating said catalytic system by burning the coke which has deposited on the surface of the catalytic system, said regeneration being conducted in air and/or oxygen, if necessary by increasing the temperature of the catalytic system to a suitable level, followed by reduction of said catalytic system with a reducing agent.

10 Claims, No Drawings

PROCESS FOR DEHYDROGENATING LIGHT PARAFFINS IN A FLUIDIZED BED REACTOR

This application is a Continuation of application Ser. No. 08/076,644, filed on Jun. 15, 19983, now abandoned.

BACKGROUND OF THE INVENTION

This invention relates to a process for dehydrogenating light paraffins, in particular $C_2$–$C_5$ (ie paraffins containing from 2 to 5 carbon atoms), in a fluidized bed to obtain the corresponding light olefins.

These form the raw material for a wide range of products such as plastics materials, synthetic rubbers, high-octane gasoline, gasoline antiknock additives, detergents etc.

In these processes the limiting factor is often the poor availability of the olefin, such as isobutene in MTBE (methyl tert-butyl ether) production.

The predicted development in the commercial demand for materials such as MTBE suggests that this limiting factor will become increasingly more critical.

The dehydrogenation reaction in question, by which such olefins are produced from widely available raw materials such as natural gas, is assuming an increasing industrial importance as it enables a considerable quantity of light olefins to be made available to the chemical industry.

Although stoichiometrically simple, the dehydrogenation reaction suffers from considerable kinetic and thermodynamic problems. The dehydrogenation reaction is characterised by an increase in the number of moles and a considerable endothermic character. In this respect, in the $C_2$–$C_{10}$ range the heat requirement of the reaction is about 27–32 kcal/mol.

This is reflected in the free energy change accompanying the reaction, which in the $C_2$–$C_5$ range remains positive to about 500° C.

A characteristic of these processes is therefore the need to operate at high temperature, ie under operating conditions at which parasite reactions are present such as skeleton isomerization, cracking and coke formation.

Consequently one of the main purposes of the catalyst is to suppress these reactions to the advantage of the dehydrogenation. Finally, the inevitable coke accumulation on the catalyst surface leads to its deactivation. Every process has therefore to include periodic catalyst regeneration.

DESCRIPTION OF THE RELATED ART

Industrial research has therefore concentrated on the important themes of development of selective catalysts, methods of heat supply to the reaction, and methods of catalyst regeneration. With regard to the first theme, catalysts have long been available in which the active principles are noble metals (supported on refractory materials such as alumina, silica or magnesium oxide [US-4438288]), or transition metal oxides (GB-2162082).

Of the noble metals, that which has received the most attention is platinum because of its high specific activity. Its importance has increased following the observation that tin, which by itself substantially inactive, is able to improve both the performance and the life of platinum-based catalysts (U.S. Pat. No. 3,998,900, U.S. Pat. No. 3,909, 451).

The yield of platinum-tin catalysts can be further improved by suitably modifying the known supports, for example with titanium (EP-441430).

With regard to the process development theme, the need to supply heat to the reaction without using furnaces for heating the feed is effectively solved by fluidized bed technology (F. Buonomo et al. Dewitt 1990 Petrochemical Review, Houston, Tex., Mar. 27–29, 1990).

The principle of this technology derives from fluid catalytic cracking (FCC).

The heart of the plant is the reactor-regenerator system. The catalyst circulates continuously from the reactor to the regenerator and vice versa.

The coke deposited on the catalyst, a reaction by-product, is burnt in the regenerator, and the heat developed, suitably supplemented by burning a suitable fuel, is stored by the solid as sensible heat.

The catalyst performs its function in the reactor and in addition transfers to the reactants the heat stored during regeneration. The plant operates continuously without the need to alternate between several reactors.

In addition to its usual role the catalyst therefore also performs the role of heat transport vehicle.

This process therefore solves the problems involved in supplying heat to the reactant system.

The catalysts used in this process have to satisfy particular requirements, the first of which is resistance to the mechanical stress deriving from their movement.

The method by which heat is supplied to the reactant system means that the operating temperature in the regenerator is considerably higher than in the reactor. The catalyst must therefore be able to withstand high temperature of the order of about 650° C. Finally, the nature of the process and the need to provide a small-dimension regenerator means that the regeneration step must be fast and simple, ie composed of the least possible number of stages.

Although platinum metal has high intrinsic catalytic activity, it has the drawback of high surface energy and therefore the tendency to form large agglomerates.

It is therefore essential to stabilize the platinum in its active form. This is achieved by distributing the metal on a suitable support. The support must have only modest interaction with platinum. This inertia in fact does not reduce the surface energy of the active principle and acts only in "statistical" terms, ie reducing the probability of two platinum crystallites meeting and fusing together, whereas excessive reactivity of the support can suppress catalytic activity.

Stabilizers and promoters such as tin are also used in addition to the support.

Finally, it should be noted that the aforesaid regeneration temperature relates to a macroscopic temperature scale. Where the coke burns, a higher local temperature is created with consequent greater thermal stress. It is known that tin also acts in the sense of reducing both the overall coke formation and the platinum area covered by the coke.

In industrial practice it has been usual to regenerate platinum-based catalysts by regeneration processes involving treatment with halogens. The drawbacks of this treatment derive essentially from the use of a toxic and corrosive substance in the form of the halogen, with a resultant design complication for the regeneration stage, which has to include the elimination of the halogen remaining on the support.

We have now found that the aforesaid drawbacks can be substantially reduced by regenerating the catalyst with suitable halogen-free gaseous streams.

SUMMARY OF THE INVENTION

The process for dehydrogenating light paraffins according to the present invention comprises reacting said paraffins with a catalytic system containing platinum, tin and an alumina support in a fluidized bed reactor, where the heat required for the reaction is provided by said catalytic system as sensible heat, operating at a temperature of between 500° and 700° C. and at a pressure of between 1 and 2 kg/cm$^2$, and regenerating said catalytic system by burning the coke which has deposited on the surface of the catalytic system, characterised in that the regeneration is conducted in air and/or oxygen, increasing the temperature of the catalytic system to a suitable level (for example by burning a suitable fuel), followed by reduction of said catalytic system with a reducing agent.

It has also been found that the formulation based on platinum, tin and aluminium can be improved by adding potassium and a lanthanide. A catalyst is then obtained able to better withstand regeneration conducted in a halogen-free atmosphere. The potassium performs the function of increasing the selectivity towards the required olefin, by moderating the isomerization side reactions.

The lanthanide, and in particular lanthanum, has various functions. It acts as a stabilizer both of the support surface and of the active principle, and moderates the acid character of the alumina, so promoting the yield of the required olefin. Finally, the lanthanide increases the heat capacity of the catalyst and, if adequately deposited on the support, also increases its resistance to impact and its density.

It is well known that lanthanum catalyzes terminal olefin bond isomerization reactions. The thermal treatment to which it is subjected is however such as to drastically reduce this activity. Specifically, the recommended catalytic system consists of:

- platinum in a quantity of between 0.05 and 1% by weight, and preferably between 0.1 and 0.3%;
- tin in a quantity of between 0.2 and 3% by weight, and preferably between 0.3 and 1.5%;
- potassium in a quantity of between 0.05 and 2% by weight, and preferably between 0.1 and 0.5%;
- an element of the lanthanide group, preferably lanthanum in a quantity of between 3 and 25% by weight, and preferably between 4 and 10%;
- alumina, reminder to 100%, the support consisting of alumina and possibly an element of the lanthanide group.

In other words the element of the lanthanide group can either be present within the support or be external to it.

Silicon in a quantity of up to 5% by weight and/or chlorides in a quantity of less than 1% by weight can also be present in the support.

If a lanthanide is present in the catalytic system it is preferable to effect the regeneration only with air.

With regard to the catalyst preparation, the support can be formed in various ways, some being described hereinafter by way of example.

A support can be obtained containing both the lanthanide and the alumina dispersed uniformly throughout the entire volume by co-precipitating respective insoluble compounds, to obtain granules for example by spray-drying and calcining the product obtained. Alternatively an alumina support can be obtained, for example by spray-drying an aluminium hydroxide suspension, to which possibly a silicon compound such as colloidal silica has been added, then calcining the solid. If required, the lanthanide can be added later to the alumina support by impregnating it with a soluble salt of the lanthanide, such as the nitrate, or precipitating an insoluble form, the drying and calcining.

Another method is to treat the alumina surface with a volatile lanthanide compound, then calcining.

Finally the lanthanide, if present, can be added either alone or simultaneously with the other components (platinum, tin and possibly potassium), in the first case it being necessary to effect a second treatment. for example impregnation by immersion or incipient wetness, to add the missing components to the system.

Some examples are given hereinafter to better illustrate the invention, which however is to no extent limited thereto.

EXAMPLES

The preferred method, used to obtain the lanthanide-based samples described in Examples 4–6 and 8–9, consists of the following stages:

a) forming the alumina-lanthanide support b) impregnating the support with a solution containing Pt/Sn(K)

c) activating the catalyst, conducted in the following manner:

a) A porous support consisting of gamma alumina, either pure or containing a certain quantity of silica, is impregnated with an aqueous solution of lanthanide nitrate, using a volume of solution equal to the pore volume.

The impregnated support is left standing for one hour, dried for one day at a temperature increasing from 50° to 120° C., and finally calcined for 135 minutes at 1000° C. in a moist air stream (for example containing 25 vol% water).

b) The support obtained is impregnated with a solution containing platinum and tin (and also possibly potassium), using the method described under point a).

To improve solute distribution over the support, a quantity of nitric or hydrochloric acid (preferably this latter) is added to the solution. As is well known, the acid acts as a competitor in the adsorption at the support surface. The impregnated solid is dried for one day at a temperature increasing from 50° to 120° C.

c) The activation is achieved by calcining the solid in a muffle furnace for 2 hours at 500° C., then reducing the calcined product for two hours at about 660° C. in a hydrogen/nitrogen stream (in a fluidized bed).

As the calcining and the reduction are conducted in different environments, the calcined product is dried for about one hour in a nitrogen stream at 150° C. before reducing.

Before evaluating its catalytic activity the sample is preconditioned by executing a complete catalytic cycle as described below.

The samples without lanthanides, described in Examples 1–3 and 7, were prepared by the method as heretofore described except for the impregnation with the aqueous lanthanide nitrate solution in stage a).

EXAMPLE 1

120 g of a sample of microspheroidal delta alumina (SA (surface area)=132 m$^2$/g) are impregnated at ambient temperature by the incipient wetness method with 56 cc of an acid solution containing 12 g concentrated HCl, 1.7 g SnCl$_2$.2H$_2$O (98%) and 0.97 g H$_2$PtCl$_6$ (25%Pt).

The impregnated substance is then dried, calcined and activated in the aforesaid manner. The final product contains 0.2 wt % Pt and 0.7 wt % Sn (the remainder being the support).

The catalyst is then tested in the reaction cycles described hereinafter, using pure oxygen as the regeneration gas.

The results are shown in Table 2.

EXAMPLE 2

120 g of a sample of microspheroidal delta alumina (SA=120 m$^2$/g) containing 1.6 wt % SiO$_2$ are treated in a manner analogous to Example 1 to give a catalyst containing 0.2 wt % Pt and 0.7 wt % Sn. The sample is tested in the reaction cycles described hereinafter, using pure oxygen as the regeneration gas.

The results are shown in Tables 1 and 2.

EXAMPLE 3

A catalyst having the same support and the same composition as that of Example 2 is tested in the reaction cycles described hereinafter using air as regeneration gas instead of pure oxygen.

The results are shown in Table 2.

EXAMPLE 4

139 g of a sample of microspheroidal gamma alumina containing 1.5 wt % SiO$_2$ are impregnated by the incipient wetness method with 65 cc of an aqueous solution containing 3.6 g of La(NO$_3$)$_3$ hexahydrate, and the impregnated substance is dried and calcined as heretofore described to give a solid containing 1 wt % La$_2$O$_3$ and an AS of 127 m$^2$/g.

120 g of this support are treated as described in Example 1 to give a catalyst containing 0.2 wt % Pt and 0.7 wt % Sn (the remainder being the support).

The catalyst is tested in the reaction cycles described hereinafter using air as regeneration gas.

The results are given in Tables 1 and 2.

EXAMPLE 5

120 g of a gamma alumina support containing 1.5 wt % SiO$_2$ and 5 La$_2$O$_3$ (SA=120 m$^2$/g), prepared by the aforedescribed method, are impregnated as described in Example 1 to give a catalyst containing 0.2 wt % Pt and 0.7 wt % Sn (the remainder being the support).

The catalyst is tested in the reaction cycles described hereinafter using air as regeneration gas.

The results are given in Tables 1 and 2.

EXAMPLE 6

120 g of a sample of gamma alumina containing 1.5 wt % SiO$_2$ and 7 wt % La$_2$O$_3$ (AS=110 m$^2$/g), prepared by the aforedescribed method, are impregnated as described in Example 1 to give a catalyst containing 0.2 wt % Pt and 0.7 wt % Sn (the remainder being the support).

The catalyst is tested in the reaction cycles described hereinafter using air as regeneration gas.

The results are given in Tables 1 and 2.

EXAMPLE 7

120 g of a catalyst analogous to that described in Example 2 are impregnated by the incipient wetness method with a solution containing 1.55 g KNO$_3$ to give a catalyst containing 0.2 wt % Pt, 0.7 wt % Sn and 0.5 wt % K (the remainder being the support). The catalyst is tested in the reaction cycles described hereinafter using oxygen as regeneration gas.

The results are given in Tables 1 and 2.

EXAMPLE 8

120 g of a sample of microspheroidal gamma alumina containing 5 wt % La$_2$O$_3$ (AS=120 m$^2$/g), prepared as heretofore described, are impregnated at ambient temperature by the incipient wetness method with 53 cc of an acid solution containing 12 g concentrated HCl, 1.7 g SnCl$_2$.2H$_2$O, 0.97 g H$_2$PtCl$_6$ (25% Pt) and 1.55 g KNO$_3$.

The impregnated substance is then dried, calcined and activated in the aforesaid manner. The final product contains 0.2 wt % Pt, 0.7 wt % Sn and 0.5 wt % K (the remainder being the support).

The catalyst is then tested in the reaction cycles described hereinafter, using air as the regeneration gas.

The results are shown in Table 2.

EXAMPLE 9

133 g of a sample of microspheroidal gamma alumina containing 1.5% SiO$_2$ are impregnated by the incipient wetness method with 62 cc of an aqueous solution containing 25.31 g Pr(NO$_3$)$_3$ pentahydrate. The impregnated substance is dried and calcined as heretofore described to give a solid containing 7 wt % Pr$_2$O$_3$ with a AS of 116 m$^2$/g.

120 g of this support are treated as described in Example 1 to give a catalyst containing 0.2 wt % Pt and 0.7 wt % Sn (the remainder being the support).

The catalyst is tested in the reaction cycles described hereinafter using air as regeneration gas.

The results are given in Tables 1 and 2.

CATALYTIC TESTS

The substances prepared in Examples 1–9 are tested in quartz fluidized bed reactors comprising a porous quartz baffle. The catalytic cycle, simulating behaviour in the industrial reactor, consists of a reaction stage in which the hydrocarbon is fed (duration 15 minutes), a stripping stage in which nitrogen is passed through to free the catalyst of absorbed products (10 minutes), a regeneration stage in which the regeneration gas is fed (oxygen, air or a mixture of the two, usually for 30 minutes), and a reduction stage under hydrogen or hydrogen/nitrogen (usually 4 minutes). The regeneration, reduction and reaction stages are separated from each other by short periods of stripping with nitrogen (5 minutes) for safety reasons as the reaction, regeneration and reduction are conducted in the same reactor. The industrial fluidized bed dehydrogenation process requires the regeneration and reduction to be carried out at a temperature higher than the reaction temperature, ie of the order of about 650° C. but depending on the reaction temperature and the specific heat of the catalyst.

The reaction temperature is a function of the reaction thermodynamics and also of the specific activity of the prepared substances. It usually varies between 540° and 580° C. for isobutane dehydrogenation (Table 1) and between 550° and 590° C. for propane dehydrogenation (Table 2).

For equal reactors, the space velocity of the reactant is a function of the activity of the prepared substances and their density, it varying in the laboratory reactors used by us from 200 to 600 Nl/lcat.h (normal liters of feeding per liter of catalysts per hour) and usually being 400 Nl/lcat.h.

The reactant flow to the reactor is controlled by a rotameter and the quantity weighed with a balance.

During the reaction and stripping stages the reactor effluent is firstly passed through a cold trap to take out the heavy products, which are weighed and tested for % carbon and % hydrogen content, and then collected in a sampling bag. The bag contents are then measured with a positive displacement pump and analyzed by gas chromatography.

Finally, after 10 minutes of stripping with nitrogen, a catalyst sample is taken to determine the quantity of coke formed. The data obtained in this manner are fed into a personal computer for calculating the material balance, conversion and selectivity towards the various products.

TABLE 1 isobutane dehydrogenation

| Example No. | HOS | T.react (°C.) | GHSV Nl/lcat · h | Convers. (%) | $iC_4H_8$ sel. (wt %) | HC sel. (wt %*) |
|---|---|---|---|---|---|---|
| 2 | 5 | 580 | 400 | 51.0 | 60.8 | 25.1 |
| 4 | 1 | 580 | 400 | 49.5 | 71.9 | 15.0 |
| 4 | 205 | 580 | 400 | 32.4 | 63.4 | 21.3 |
| 5 | 8 | 560 | 400 | 49.9 | 75.1 | 11.8 |
| 6 | 1 | 580 | 420 | 60.1 | 73.2 | 12.0 |
| 6 | 4 | 560 | 420 | 55.1 | 77.4 | 10.7 |
| 6 | 199 | 580 | 400 | 56.0 | 75.0 | 12.5 |
| 7 | 12 | 580 | 400 | 42.3 | 83.3 | 1.2 |
| 8 | 1 | 580 | 400 | 51.1 | 83.5 | 3.5 |
| 8 | 199 | 580 | 400 | 36.7 | 86.3 | 1.7 |
| 9 | 4 | 580 | 400 | 49.1 | 75.5 | 11.6 |
| 9 | 195 | 580 | 400 | 48.7 | 78.5 | 10.2 |

(*)HC = $C_4H_{10}$ n-$C_4H_8$ 2cis-$C_4H_8$ 2trans-$C_4H_8$

The HOS (hours on stream) data shown in the table do not take account of the complete preconditioning catalytic cycle.

TABLE 2 propane dehydrogenation

| Example No. | HOS | T.react (°C.) | GHSV Nl/lcat · h | Convers. (%) | $C_3H_6$ select. (wt %) |
|---|---|---|---|---|---|
| 1 | 1 | 590 | 400 | 37.7 | 71.0 |
| 1 | 8 | 590 | 400 | 38.0 | 70.0 |
| 2 | 1 | 590 | 400 | 39.9 | 86.5 |
| 2 | 200 | 590 | 400 | 36.9 | 88.9 |
| 3 | 1 | 590 | 400 | 40.1 | 85.6 |
| 3 | 196 | 590 | 400 | 31.2 | 83.7 |
| 4 | 1 | 590 | 400 | 39.8 | 85.0 |
| 4 | 199 | 590 | 400 | 30.9 | 86.2 |
| 5 | 2 | 580 | 400 | 39.3 | 85.4 |
| 6 | 1 | 590 | 400 | 41.5 | 85.9 |
| 6 | 197 | 590 | 400 | 42.0 | 84.9 |
| 7 | 1 | 590 | 400 | 37.5 | 86.4 |
| 8 | 1 | 590 | 400 | 39.1 | 85.4 |
| 8 | 198 | 590 | 400 | 33.1 | 87.2 |
| 9 | 1 | 590 | 400 | 40.3 | 87.5 |
| 9 | 198 | 590 | 400 | 39.0 | 87.2 |

The HOS (hours on stream) data shown in the table do not take account of the complete preconditioning catalytic cycle.

We claim:

1. A process for dehydrogenating $C_2$–$C_5$ paraffins to obtain in corresponding olefins, comprising reacting said paraffins with a catalytic system containing platinum, tin, an element of the lanthanide group and an alumina support in a fluidized bed reactor, where the heat required for the reaction is provided by said catalytic system as sensible heat, operating at a temperature of between 500° and 700° C. and at a pressure of between 1 and 2 kg/cm², and regenerating said catalytic system by burning coke which has deposited on a surface of catalytic system, wherein the regeneration is conducted in air, optionally by increasing the temperature of the catalytic system, followed by reduction of said catalytic system with a reducing agent and wherein said catalytic system consists of:

0.05–1% by wt. platinum, 0.2–3% by wt. tin, 3–25% by wt. of an element of the lanthanide group, the remainder being alumina and, optionally, up to 5% by wt. silica and up to less than 1% by wt. chlorides.

2. A process as claimed in claim 1, wherein the support portion of said system consists of alumina or alumina and an element of the lanthanide group.

3. A process as claimed in claim 1, wherein the support portion of said system consists of alumina, optionally an element of the lanthanide group, optionally up to 5% by wt. silica and optionally up to less than 1% by wt. chlorides.

4. A process for dehydrogenating $C_2$–$C_5$ paraffins to obtain corresponding olefins, comprising reacting said paraffins with a catalytic system containing platinum, tin, a lanthanide and an alumina support in a fluidized bed reactor, where the heat required for the reaction is provided by said catalytic system as sensible heat, operating at a temperature of between 500° and 700° C. and at a pressure of between 1 and 2 kg/cm², and regenerating said catalytic system by burning coke which has deposited on a surface of the catalytic system, wherein the regeneration is conducted in air, optionally by increasing the temperature of the catalytic system, followed by reduction of said catalytic system with a reducing agent and wherein said catalytic system consists of:

0.05–1% by weight platinum, 0.2–3% by weight tin, 3–25% by weight of an element of the lanthanide group, 0.05 to 2% by weight potassium, the remainder being alumina.

5. A process as claimed in claim 1, wherein the element of the lanthanide group is lanthanum.

6. The process as claimed in claim 3, wherein the element of the lanthanide group is lanthanum.

7. The process as claimed in claim 4, wherein the element of the lanthanide group is lanthanum.

8. A process as claimed in claim 4, wherein the platinum is present in a quantity of between 0.1 and 0.3% by weight, the tin in a quantity of between 0.3 and 1.5% by weight, the potassium in a quantity of between 0.1 and 0.5% by weight, and the element of the lanthanide group in a quantity of between 4 and 10% by weight.

9. A process as claimed in claim 3 wherein said catalyst is prepared by impregnating microspheriodal gamma alumina containing 1.5 weight percent $SiO_2$ with an aqueous solution containing $La(NO_3)_3$ by the incipient wetness method, drying and calcining followed by impregnation of an acid solution of $SnCl_2.2H_2O$ and $H_2PtCl_6$ by the incipient wetness method.

10. The process as claimed in claim 4, wherein said element of the lanthanide group is lanthanum.

* * * * *